United States Patent [19]

Tsang et al.

[11] 4,224,279
[45] Sep. 23, 1980

[54] REACTIVE GAS GENERATOR

[75] Inventors: Wing Tsang, Gaithersburg; James A. Walker, Rockville, both of Md.; Douglas W. Cornell, Glen Rock, N.J.

[73] Assignee: The United States of America as represented by the Secretary of Commerce, Washington, D.C.

[21] Appl. No.: 913,918

[22] Filed: Jun. 8, 1978

Related U.S. Application Data

[62] Division of Ser. No. 755,912, Dec. 30, 1976, abandoned.

[51] Int. Cl.³ .......................... G01N 1/22; G01N 1/26
[52] U.S. Cl. ................................ 422/78; 23/230 PC; 23/232 R; 73/421.5 R; 422/129; 422/130
[58] Field of Search ....................... 23/230 PC, 232 R; 422/78, 129, 130; 73/421.5 R

[56] References Cited

U.S. PATENT DOCUMENTS

| 3,403,978 | 10/1968 | Favre | 422/78 |
|---|---|---|---|
| 3,518,059 | 6/1970 | Levy | 422/78 |
| 3,740,195 | 6/1973 | Leitzau | 23/232 R |
| 3,847,546 | 11/1974 | Paul | 422/78 |
| 4,087,249 | 5/1978 | Okumoto et al. | 422/78 |

OTHER PUBLICATIONS

Tsang et al., "A Simple Technique for the Generation of Dilute Mixtures of Pollutant Gases", Journal of Research, N.B.S., A. Physics & Chem. vol. 78A, No. 2, Mar.-Apr. 1974.

Primary Examiner—R. E. Serwin
Attorney, Agent, or Firm—Eugene J. Pawlikowski; Alvin J. Englert

[57] ABSTRACT

A dilute mixture of a large organic parent compound in an inert diluent is formed using a specially designed diffusion cell to control the amount of parent compound that is taken up by the diluent gas. The dilute mixture flows through a hot pyrolyzing tube where the parent compound is decomposed solely and totally by a gas phase unimolecular reaction into equimolar amounts of reactive gas and a stable reaction product. The method produces an internal standard for determining the concentration of the reactive gas since the stoichiometry of the reaction requires that the concentration of the reactive gas be equal to the concentration of the other reaction product, which can be easily calibrated by standard methods.

11 Claims, 7 Drawing Figures

REACTIVE GAS GENERATOR

This is a division of application Ser. No. 755,912 filed Dec. 30, 1976 and now abandoned.

FIELD OF THE INVENTION

The present invention relates to chemical analysis such as the generation of reactive gases for analytical laboratory use and more particularly to the production of accurate and precise quantities of reactive gases over wide concentration ranges using a gas diffusion cell with a pyrolyzer.

BACKGROUND OF THE INVENTION

Laboratory studies in pollution chemistry, occupational health hazards and toxicology require the continuous generation of accurately known quantities of reactive gases in dilute concentration. Such reactive gases are needed for the calibration of measuring instruments, to evaluate analytical methodology, to carry out toxicity investigations and in physico-chemical studies on the rate of mechanisms of pollutant formation.

The reactive nature of the gases makes standard static methods for preparation of the gases unsatisfactory so that a dynamic method is needed where the required samples are prepared immediately before use. U.S. Pat. No. 3,740,195 discloses a continuous reactive gas generator which uses a moving metal ribbon coated with a pyrolyzable salt. However, this device uses a non-volatile salt and would not work with a volatile organic liquid which would be vaporized before introduction into the pyrolysis zone. In addition, pyrolysis of a solid often gives variable and irreproducible results. Furthermore, the use of a salt as a parent compound is not versatile since the types of thermally stable reactive gases which can be generated from salts if quite limited.

The paper "Pyrolysis Generation of Dilute Concentration of Sulphur Dioxide" in Analytical Chemistry, Vol. 46, page 933, June 1974 discloses a sample tube in combination with a pyrolyzing tube. The sample tube contains the pyrolyzable parent compound and is enclosed in an oven. Carrier gas is passed over the compound in the sample tube. This approach was selected in preference to the use of a diffusion cell for the following reasons: (a) The pyrolytic decomposition process must be carried out in the total absence of air. In the usual diffusion cells this is not achievable because even the slightest leak will throw off the results. (b) Standard diffusion cells are monolithic (no joints or valves, etc.) and are made of glass. Such a construction is very difficult to work with.

The publication "A Simple Technique for the Generation of Dilute Mixtures of Pollutant Gases", Journal of Research of the National Bureau of Standards, Vol. 78A, No. 2, page 157, March-April, 1974, discloses a simple quantitative means of generating dilute mixtures of formaldehyde, acetaldehyde and acrolein by the pyrolysis of compounds the decomposition of which produce equal numbers of reactive and stable molecules. However, a pulse technique is used and this limits its range of potential applications. For toxicity and physico-chemical investigations continuous generation is essential; even for calibration purposes continuous generation is more effective because it more closely simulates the situation being studied.

The prior art shows methods for the production of small concentrations of reactants including precision flow dilution systems and permeation tubes. But the accuracy of these methods depends critically on the skill in preparing the sample or setting reaction conditions. Further, they do not work well over a wide range of concentrations.

Thus, there continues to exist in the art the need for means for the continuous generation of accurately known quantities of reactive gases in dilute concentrations, and the problem is particularly difficult because the desired gases are reactive yet must be obtained in dilute concentrations.

SUMMARY OF THE INVENTION

It is, accordingly, an object of the present invention to provide for improved chemical analysis.

It is another object to overcome the deficiencies of the prior art, such as indicated above.

It is yet a further object to the present invention to provide for the improved assessment of environmental and occupational health hazards, for the improved calibration of measuring instruments, for the evaluation of analytical methodologies, and/or for the carrying out of toxicity investigations.

It is another object of the present invention to provide for the improved generation of reactive gases in dilute concentrations.

It is a further object to provide a generator capable of producing accurate and precise quantities of reactive gases over wide concentration ranges.

It is another object to provide dynamic and continuous production of the reactive gases immediately at the time needed.

It is an object of the invention to produce a gas generator in which it is easy to change the concentration of the reactant being produced.

It is an object of the invention to produce a gas generator which can be selectively applied to the generation of a great variety of reactive gases by the selection of a suitable parent molecule to produce each desired reactant.

It is another object to provide a device whose accuracy is not critically dependent on the skill of the operator.

It is a further object to use a method in which the reaction variables need not be critically controlled to produce accurate results.

It is an additional object of the present invention to use a system which has an internal calibration standard so that the reactant concentration can always be accurately determined without regard to the measurement of external variables.

The present invention involves a method and a device to prepare reactive gases in accurate and precise quantities over wide concentration ranges by first producing a dilute mixture of a relatively large organic parent molecule in an inert diluent through the use of a specially designed diffusion cell and then flowing this mixture through a hot pyrolyzing tube where stoichiometric decomposition occurs and the reactant gas of interest is formed. The parent molecule undergoes pyrolytic decomposition solely and totally by a gas phase unimolecular reaction into equimolar amounts of the reactive gas and a stable hydrocarbon.

Basically, the generator is made up of two constant temperature compartments. The first contains a metal diffusion cell and a buffer cell with a flexible heater and a temperature controller. The second contains a pyrolyzer preferably made of ⅛ inch outside diameter tubing with a cartridge heater for thermal input and a thermostat. The preferred material for the pyrolyzer tube is gold since gold is relatively inert and does not catalyze surface reactions.

The diffusion cell limits the uptake of sample by the carrier gas. The diffusion rate depends on the diffusion tube cross-section and the cell temperature so that the diffusion rate may be varied by changing these physical parameters. The concentration of reactive gas produced is directly proportional to the diffusion rate and inversely proportional to the flow rate. The present invention has been used to generate formaldehyde, acetaldehyde, acrolein, sulphur dioxide, hydrogen cyanide and hydrogen chloride. However, most thermally stable reactive gases can be generated in this manner.

BRIEF DESCRIPTION OF THE DRAWING

The invention will be better understood from the detailed description of various embodiments cited for the sake of illustration with reference to the accompanying drawings in which.

DETAILED DESCRIPTION OF THE PREFERRED EMBODIMENTS

Figure 1:
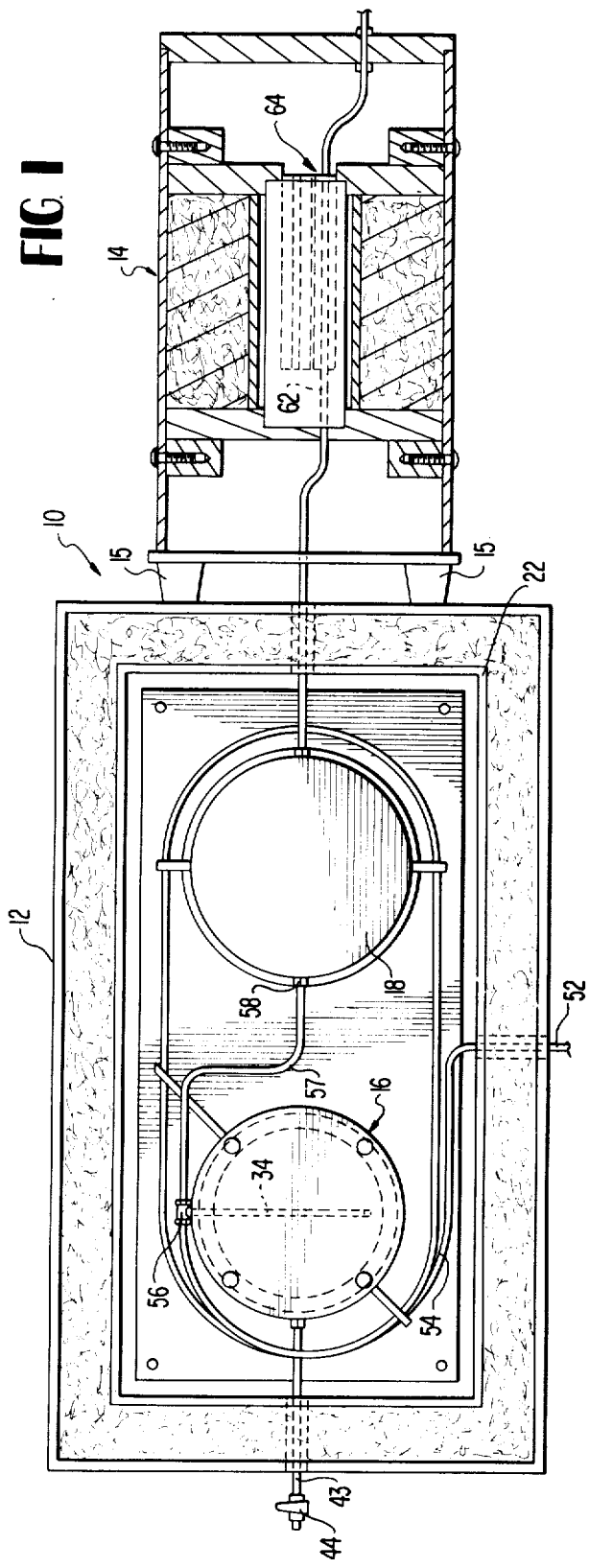
FIG. 1 is a top plan view partially in section of the diffusion cell and pyrolyzer of an embodiment of the invention.
Figure 2:
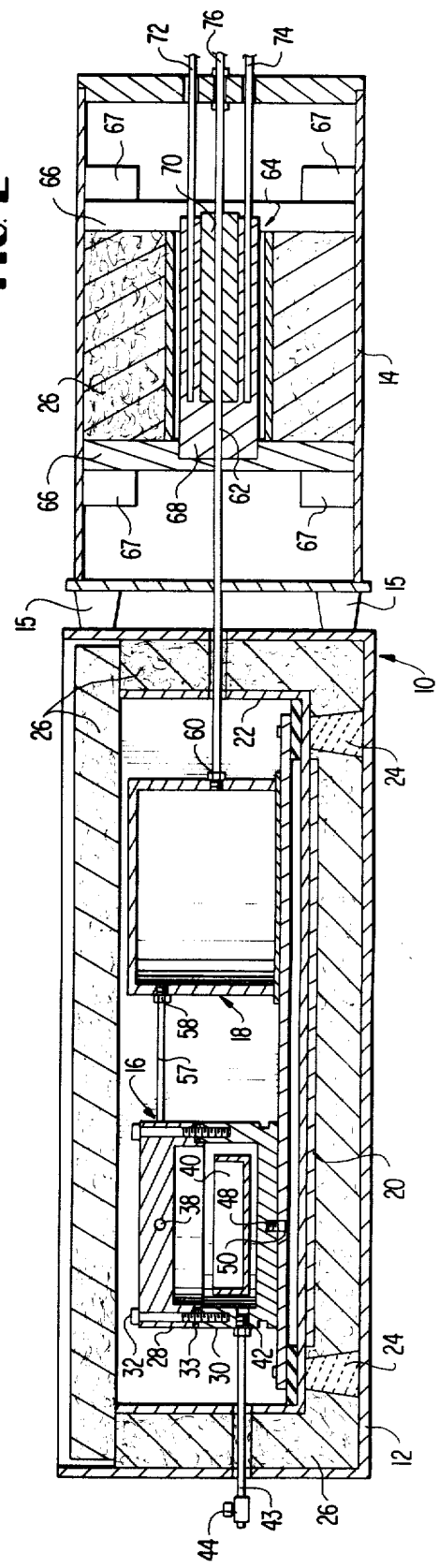
FIG. 2 is a side elevational view partially in section of the diffusion cell and pyrolyzer.

A reactive gas generator 10 as shown in FIGS. 1 and 2 comprises two separate compartments, i.e., a diffusion cell outer box 12 and a pyrolyzer housing 14 connected together rigidly by insulators 15. The diffusion cell compartment 12 contains an inner box 22 which contains a diffusion cell 16 and buffer cell 18. The inner box 22 is mounted inside the outer box 12 through ceramic insulators 24 or the like and is surrounded by suitable insulation 26. A heater 20 is fixed to the bottom outside surface of inner box 22. A controller e.g., a thermostat, not shown, is used to maintain constant temperature in a known manner.

Figure 3:
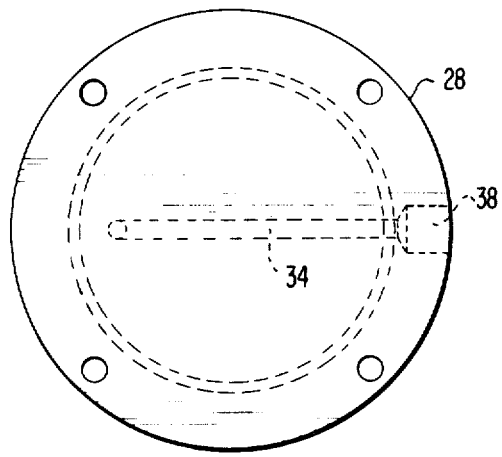
FIG. 3 is a top plan view, partially in section, of the diffusion cell head.
Figure 5:
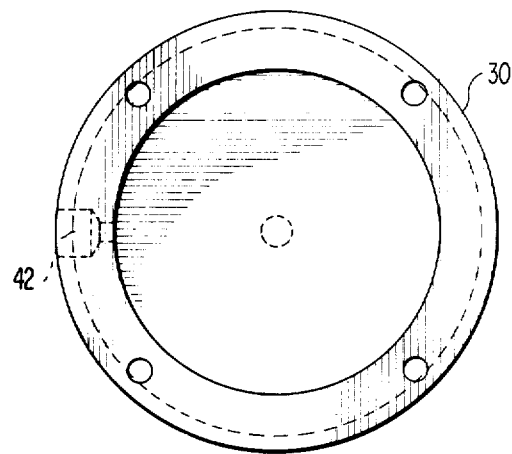
FIG. 5 is a top plan view, partially in section, of the diffusion cell base.
Figure 4:
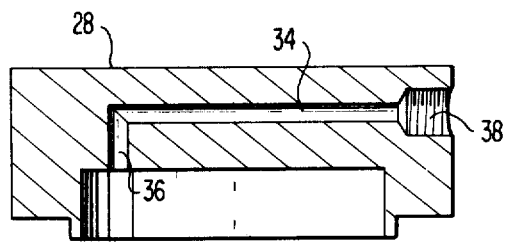
FIG. 4 is a side elevational view, partially in section, of the diffusion cell head.
Figure 6:
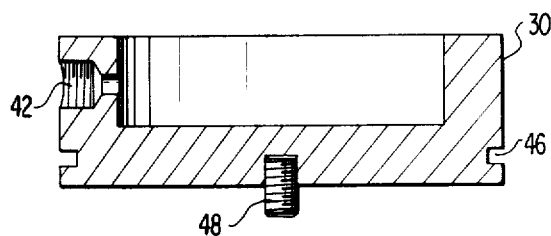
FIG. 6 is a side elevational view, partially in section, of the diffusion cell base.

The diffusion cell 16 is made up of an upper portion or head 28 as shown in FIGS. 3 and 4 and a lower portion or base 30 as shown in FIGS. 5 and 6. The head 28 has a diffusion hole 38 which opens into diffusion column 34 which runs horizontally through the head and ends in a vertical column portion 36 which opens into the interior cavity of the diffusion cell. The parent substance to be pyrolyzed, in liquid or solid form, is placed in a glass cup 40 which sits in the base 30 of the diffusion cell. The head 28 and base 30 of the diffusion cell are sealed tightly together using a gasket 33 and are held together by cap screws 32. The base 30 has a purge hole 42 to which is connected a tube 43 with a purge valve 44 to permit purging of air from the diffusion cell 16 so that no oxidation will occur to interfere with the pyrolytic process. The base 30 has a groove 46 around its lower circumference so that it may be held by hold-down clamps, and an alignment pin 48 which fits into the alignment hole 50 on the bottom of the inner box 22 for placing the cell in its proper position.

A tank, not shown, of a suitable carrier gas is connected through a diluent gas inlet 52 to a tubing 54 which makes one complete loop around the inner box 22 before passing through a dilution T-connection 56 which is connected, in turn through the diffusion hole 38 to the diffusion column 34, 36 and to the interior of the diffusion cell. As the carrier gas flows through the dilution T-connection 56, it picks up a quantity of a vaporized parent substance at a rate determined by the cross-sectional area of the diffusion column and the temperature of the cell. From the dilution T-connection 56 the dilute mixture of parent substance vapor in the carrier gas flows through a tubing 57 to the buffer cell 18 entering through a buffer cell connector 58. The buffer cell 18 functions to take out pressure surges that arise from the switching of valves or the connection of fittings. The entire system is operated at about one-half atmosphere above ambient pressure (e.g., about 22 psia). Control is effected by means of a needle valve, not shown, at the exit of the pyrolyzer.

The dilute mixture flows from the buffer cell 18 through an output connector 60 and into a pyrolyzing tube 62 of a pyrolysis furnace 64 within the pyrolyzer housing 14. The pyrolysis furnace 64 comprises the pyrolyzing tube 62 surrounded by a cartridge heater 70 held in a heater block 68 with a temperature sensor 72 and a temperature controller 74. The pyrolysis furnace 64 is mounted on one or more block supports 66 which are fastened to the pyrolyzer housing 14 through mounts 67. The pyrolysis furnace 64 is surrounded by suitable insulation 26. The reactive gas mixture produced in the pyrolyzer then flows through the exit tube 76 which has a needle valve (not shown).

Figure 7:
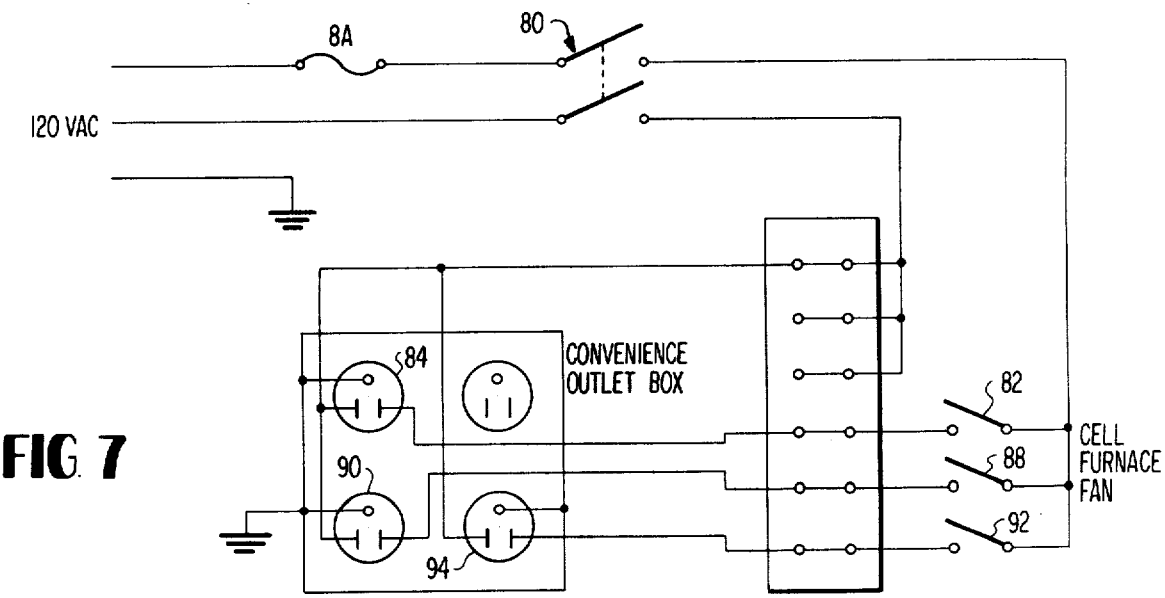
FIG. 7 is a wiring diagram for the reactive gas generator.

The electrical connections of the gas generator unit are shown in FIG. 7. The main power switch 80 is in series with and ahead of the other switches. The cell heater switch 82 controls the outlet 84 for the cell temperature controller and cell heater. Furnace switch 88 controls outlet 90 for the furnace temperature controller and heater and cooling fan swith 92 controls an outlet 94 for the cooling fan. The main power, cell heater and furnace heater, switches should be turned on a few hours before use with the cell and furnace temperature controllers set at the desired temperatures to allow the system to come to equilibrium.

A suitable parent molecule is one in which the expected stoichiometry will occur under all reaction conditions. Thus the flow rate and furnace temperature need not be closely controlled. The concentration of the reactive gas produced and also of the hydrocarbon reaction product depends on the concentration of the parent molecule, the reaction time and the temperature, and can be determined from these factors. But more importantly, the stoichiometry of the reaction requires that the concentration of the reactive gas equals the concentration of the hydrocarbon products so that a determination of the concentration of the hydrocarbon will give the concentration of the reactive gas. Regardless of the values of the operational variables that control or determine the absolute concentration, the concentration of the hydrocarbon can be easily determined by standard calibration techniques.

Thus, this method has a built-in internal standard from which the reactive gas concentration can always be accurately measured thereby eliminating the criticality of preparing the sample and for setting reaction conditions. However, for this method to be accurate, it is important to avoid surface or chain-induced decomposition processes of the hydrocarbons since they are irreproducible and would give an unreliable calibration of the hydrocarbon produced.

Furthermore, by varying the quantity of the parent molecule diffusing into the inert diluent, this method has for practical purposes an infinite dynamic range. The design of the present invention is such that the same instrument can generate a wide variety of reactive gases since it can operate with any suitable parent molecule. The system accuracy is independent on the skill of the operator in preparing the sample or setting the reaction conditions.

DESCRIPTION OF OPERATION

In operation, the cabinet is opened to gain access to the cell compartment. The diffusion cell head is removed so that the glass dish can be filled with, for example, about 15 grams or 15 cc of the parent compound. The diffusion cell head is then replaced. Of course, a head with the appropriate diffusion tube cross-section can be selected to give the desired diffusion rate. Diffusion columns with I.D. up to 0.25 in. my be used, with 0.125 in. generally used.

The cylinder of diluent carrier gas is connected to the inlet. The gas cylinder has a two stage regulator. Helium is used as the carrier gas, but any other non-reactive gas may be used, such as argon or even nitrogen depending on the nature of the reactive gas generated. The valve on the diluent gas cylinder is opened and the pressure regulator is set to a value at or near 25 psig. The micrometer is opened and the purge valve is opened for about 15 minutes to allow the cell to be entirely purged of oxygen. After the purge valve is closed, the micrometer and cylinder pressure are adjusted to give a flow of 40 cc/minute and a system pressure of about 7 psig. A flow calibration curve is provided to give approximate settings; a bubble flowmeter could be used for greater accuracy. Flow rates from 10 to 200 cc/minute can be used.

All connections are then checked for leaks, either with soap bubbles or with a leak detector. When all leaks have been eliminated, the cell compartment is closed. Then the power cord is plugged in and the main power, cell heater and furnace heater switches are turned on. The temperature controllers are set to the desired temperatures, allowing about 2 hours for the system to equilibrate, with the carrier gas continuously flowing.

The compartment containing the diffusion and buffer cells can be maintained at constant temperatures from ambient to 250° C., with temperature control of ±0.1° C. The pyrolyzer compartment contains a cartridge heater for thermal input in the range from 0 to 760° C., with temperature control of ±12° C. The pyrolyzer is operated at a high enough temperature to ensure complete pyrolysis of the parent compound.

The proper selection of the diffusion column cross-section and the cell compartment temperature, which is held to narrow limits, allows the use of many different parent compounds. Further, it allows for the easy and continuous setting of the diffusion rate over a wide range. The selection of the diffusion rate and the flow rate of the carrier gas control the concentration of the parent compound in the carrier gas, and thus of the reactive gas produced.

Selection of a suitable parent compound according to the present invention to produce a desired gas will be within the skill of the art; thus formaldehyde is produced using 3-methyl-3-buten-1-ol as the parent compound; acetaldehyde using 4-penten-2-ol; acrolein using 5-methyl-1,5-hexadien-3-ol; hydrogen cyanide using ethylcyanoformate; sulphur dioxide using trimethylene sulfone and hydrogen chloride using cyclohexyl chloride. Of course, the present invention is not limited to producing just these reactive gases. Rather it is readily adaptable to produce any reactive gas from a suitable parent compound. Other experiments indicate that allyl methyl ether or formalin may be used as the parent compound for formaldehyde; allyl ethyl ether or 3-pentene-2-ol for acetaldehyde; and oxacyclohexene-2 for acrolein. Similar reactions can be used to generate a variety of other gases, including organic acids, alcohols, ketones, hydrogen halides and ammonia. Some typical reactions which can be utilized are suggested in "A Simple Technique for the Generation of Dilute Mixtures of Pollutant Gases", supra:

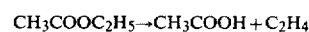

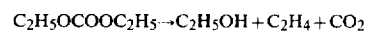

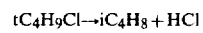

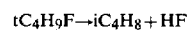

A large number of possible parent compounds and reactive gases that can be produced from these are suggested in the publication Benson and O'Neal, Kinetic Data on Gas Phase Unimolecular Reactions, Nat. Stand. Ref. Data Ser., Nat. Bur. Stand. (U.S.) 21, 645 pages (February 1970).

EXAMPLES

Specific results have been reported in publication NBSIR 76-1000 "The Construction, Operation and Performance of a Reactive Gas Generator; with Specific Application to HCHO, CH$_3$CHO, CH$_2$CHCHO, SO$_2$, HCN and HCl Production", U.S. Department of Commerce, National Bureau of Standards, January 1976.

Formaldehyde is generated by the decomposition reaction CH$_2$=C(CH$_3$)CH$_2$CH$_2$OH→iC$_4$H$_8$+HCHO. The validity of the postulated stoichimetry is established by gas chromatographic analysis. The resulting area ratio over the applicable range, where the formaldehyde was first converted to methane for measurement purposes, is 4.22±0.12 to 1. The departure from exact 4 to 1 dependence is attributed to a substantial tailing in the formaldehyde peak making complete integration difficult. Maximum thru-put (100% conversion) in terms of formaldehyde output per minute as a function of cell temperature is given by least squares analysis of the data yields at 7.4 psig and over the temperature range of 30°-90° C. as log$_{10}$ [μg. HCHO/minute]=−2704.8[1/T]+9.09±0.09.

The thru-put rate is 2 to 50 μg/minute. The standard deviation or "settability" is 4%. With flow rates of 20–200 cc/minutes, the pyrolyzer temperatures necessary to insure close to 100% conversion range from 600° to 680° C. The long term stability of formaldehyde generation and the dynamic range of the concentration as a function of flow rate and of pressure are shown in the following Tables:

TABLE I (a) Long term behavior of formaldehyde generation. Cell temperature 40° C. Flow rate=30 cc/min. Pyrolyzer at 650° C. System pressure=7.2 psig.

| Hours | Concentration |
| --- | --- |
| 0 | 75 ppm |
| 2 | 75 ppm |
| 6 | 74 ppm |
| 72 | 76.5 ppm |

(b) Variation of HCHO concentration as a function of flow rate at 88° C. 7.5 psig cell pressure. Pyrolyzer temperature 675° C.

| Flow rate (cc/min.) | (Flow rate)$^{-1}$ Min/cc | ppm HCHO |
| --- | --- | --- |
| 33.2 | .0301 | 881 |
| 81.0 | .0124 | 397 |
| 210.0 | .0048 | 148 |

(c) Variation of HCHO concentration as a function of pressure at 88° C.; 210 cc flow rate, pyrolyzer temperature at 655° C.

| Pressure (psia) | ppm HCHO |
| --- | --- |
| 26.4 | 122 |
| 22.1 | 148 |
| 18.3 | 172 |

Acetaldehyde is generated by the decomposition reaction $CH_2=CHCH_2CH(OH)CH_3 \rightarrow C_3H_6 + CH_3CHO$. The ratio of the areas of the propylene to acetaldehyde peaks is 2.89±0.05 to 1 by gas chromotographic analysis, which establishes the stoichiometry of 3 to 1 expected. Maximum thru-put (100% conversion) in terms of acetaldehyde output/min. as a function of cell temperature is given by least squares analysis at 7.0 psig over the temperature range of 30°-90° C. as $\log_{10}[\mu g\ CH_3CHO/min.] = (-2814 \pm 30)[1/T] + 9.86 \pm 0.09$. The thru-put range is thus 4-100 g/min. The standard deviation is ±4% [and with internal standard accuracy is increased by a factor of 2 or more]. For flow rates of 20 to 100 cc/min. the pyrolyzer temperature for complete conversion is from 650° to 700° C. The long term stability is shown in the following Table:

TABLE II

Long term behavior of acetaldehyde generator at 30.2° C. Flow rate=40 cc/min. Pyrolyzer at 680° C. System pressure=7.0 psig.

| Hours | Concentration | |
| --- | --- | --- |
| 0 | 56 | ppm |
| 96 | 58 | ppm |
| 120 | 58.5 | ppm |
| 168 | 56.5 | ppm |

These and other experiments with the gas generator show the "settability" or accuracy of the instrument, the long term stability and the wide dynamic range of concentrations.

Other embodiments and adaptations may be provided without going beyond the scope of the invention. It will be obvious to those skilled in the art that various changes may be made without departing from the scope of the invention and the invention is not to be considered limited to what is described in the specification.

What is claimed is:

1. A reactive gas generator for use in generating known stable quantities of reactive substances continuously and in dilute, substantially invariant concentrations to permit calibrating of measuring instruments, toxicity measurements and pollutant formation rate measurement, the generator comprising:

diffusion cell means for generating a dilute gaseous mixture of an organic parent compound in an inert diluent, said diffusion cell means comprising a metal diffusion cell for holding said organic parent compound, heating means to vaporize said organic compound, a diffusion column in the head of the diffusion cell to allow said parent compound vapor to diffuse from said diffusion cell, a diffusion tee connected to said diffusion column wherein said parent compound vapor is mixed with the diluent gas to form a dilute mixture and tubing to carry said diluent gas from a tank to said diffusion tee where it picks up the parent compound vapor;

further tubing to carry said mixture from said diffusion cell means;

pyrolyzer means coupled to said diffusion cell means by said further tubing to receive the mixture therefrom for producing a complete stoichiometric decomposition of said compound to form said reactive gas; and means coupled to said pyrolyzer means for allowing exit of the reactive gas therefrom continuously in dilute, substantially invariant concentrations.

2. A reactive gas generator as claimed in claim 1 wherein a buffer cell is included between said diffusion tee and said pyrolyzer means to remove pressure surges.

3. A reactive gas generator as claimed in claim 1 wherein said pyrolyzer means comprises:

a gold tube wherein said parent compound is totally decomposed to produce said reactive gas;

heater means to provide the heat input to completely pyrolyze said parent compound;

temperature controller means to set the desired temperature, said temperature being high enough to cause total decomposition of said parent compound; and temperature sensor means.

4. A reactive gas generator as claimed in claim 1 wherein said pyrolyzer means comprises a pyrolyzer for effecting pyrolytic decomposition of the parent compound solely and totally by a gas phase phase unimolecular reaction into equimolar amounts of reactive gas and a stable compound.

5. A reactive gas generator as claimed in claim 1 including present in said diffusion cell means, as the organic parent compound, a quantity of 3-methyl-3buten-1-ol, the reactive gas produced in said pyrolyzer means being formaldehyde.

6. A reactive gas generator as claimed in claim 1 including present in said diffusion cell means, as the organic parent compound, a quantity of 4-penten-2-ol, the reactive gas produced in said pyrolyzer means being acetaldehyde.

7. A reactive gas generator as claimed in claim 1 including present in said diffusion cell means, as the organic parent compound, a quantity of 5-methyl-1, 5-hexadien-3-ol, the reactive gas produced in said pyrolyzer means being acrolein.

8. A reactive gas generator as claimed in claim 1 including present in said diffusion cell means, as the organic parent compound, a quantity of ethylcyanoformate, the reactive gas produced in said pyrolyzer means being hydrogen cyanide.

9. A reactive gas generator as claimed in claim 1 including present in said diffusion cell means, as the organic parent compound, a quantity of trimethylene sulfone, the reactive gas produced in said pyrolyzer being sulfur dioxide.

10. A reactive gas generator as claimed in claim 1 including present in said diffusion cell means, as the organic parent compound, a quantity of cyclohexyl chloride, the reactive gas produced in said pyrolyzer means being hydrogen chloride.

11. A reactive gas generator according to claim 1, wherein said diffusion cell comprises:
- a metal base, which contains a glass dish of an organic parent compound;
- a metal head which is fastened tightly to said metal base by means of cap screws, with a tight seal being formed along a gasket; and
- a diffusion hole in said head to the outside; and wherein
- said diffusion column runs horizontally through the head, with one end opening into said diffusion hole, and the other end opening into a vertical column segment opening into the interior of said diffusion cell; and
- a purge hole in said base, said purge hole leading to a tube with a purge valve to allow said diffusion cell to be purged of air before use.

* * * * *